(12) United States Patent
Testa et al.

(10) Patent No.: US 6,394,799 B1
(45) Date of Patent: May 28, 2002

(54) APPARATUS FOR POSITIONING THE MANDIBULAR JAWS

(75) Inventors: Mauro Testa, Avigliano; Felice Festa, Formia, both of (IT); William C. Machata, Hartford, WI (US)

(73) Assignee: Micerium S.r.l. (IT)

( * ) Notice: Subject to any disclaimer, the term of this patent is extended or adjusted under 35 U.S.C. 154(b) by 0 days.

(21) Appl. No.: 09/568,842

(22) Filed: May 11, 2000

(30) Foreign Application Priority Data

May 11, 1999 (IT) ......................... SV99A0013

(51) Int. Cl.⁷ .................................. A61C 7/00
(52) U.S. Cl. ........................................ 433/19
(58) Field of Search ................. 433/19, 7, 18

(56) References Cited

U.S. PATENT DOCUMENTS

| | | | |
|---|---|---|---|
| 1,597,529 A | * 8/1926 | Leonard ........................ | 433/19 |
| 4,597,738 A | * 7/1986 | Sander et al. .................. | 433/7 |
| 5,443,384 A | * 8/1995 | Franseen et al. ............... | 433/18 |
| 5,848,891 A | * 12/1998 | Eckhart et al. ................ | 433/19 |

FOREIGN PATENT DOCUMENTS

SU    1680139 A1    9/1991

* cited by examiner

*Primary Examiner*—Todd E. Manahan
*Assistant Examiner*—Melba Bumgarner
(74) *Attorney, Agent, or Firm*—Foley & Lardner (57) ABSTRACT

Apparatus for the correction of the relative position between the maxillary and the mandibular jaws comprises a first guiding element and a second guiding element. The two guiding elements are mounted in a position lateral to the corresponding dental arch by means of anchoring elements. The two guiding elements are initially disengaged from each other and come together to cooperate only from a pre-set intermediary position of closure of the mandibular jaw toward the maxillary jaw. The two guiding elements constructed so that, from the intermediate closure position, they come into reciprocal contact and form contact surfaces with relative sliding movement. Upon closure of the jaws, the cooperating contact between the two guiding elements exerts automatically a push in a direction of the relative displacement of the maxillary jaw and the mandibular jaw for the assuming of the correct relative position between the maxillary jaw and the mandibular jaw.

29 Claims, 10 Drawing Sheets

APPARATUS FOR POSITIONING THE MANDIBULAR JAWS

FIELD OF THE INVENTION

The invention has as its object an apparatus for the correction of the relative position between the maxillary and the mandibular jaws. The apparatus comprises a first guiding element and a second guiding element, with the two elements initially disengaged from each other when the jaws are in an open position. The two guiding elements come together in cooperating contact when the maxillary and mandibular jaws are between a pre-set intermediate closure position and a complete closure position. The two elements are mounted in lateral position in correspondence with the dental arch by means of fasteners.

BACKGROUND OF THE INVENTION

There are presently known devices of this construction, in which the two elements come into reciprocal contact that prevents the patient from completely closing the mandibular jaw against the maxillary one when the two jaws are in an incorrect position. Generally, the correction relates to relative positioning of the mandibular and the maxillary jaws in the antero-posterior direction; that is, they relate to a forward displacement or to a backward displacement of the mandibular jaw relative to the maxillary jaw, with respect to the correct closure position.

The two reciprocally stopping elements compel the patient to consciously move his mandibular jaw into the correct position when he wishes to close that jaw against the maxillary one. Otherwise, the two stops keep the mandibular jaw at a certain distance from the maxillary one, preventing the closure and therefore the mastication.

Such a device therefore is a passive device, and it depends on the patient correcting the position of his own free will to set forth the function of mastication, for example, or simply to close his mandibular jaw against his maxillary jaw. There is therefore no control of the correction, whether to ensure that the same occurs safely, or to make sure that the forward or backward displacement takes place progressively, accustoming the patient to assume the correct mandibular position. Furthermore, the known apparatuses are not capable of also guaranteeing the arising of pressure in directions different from the antero-posterior ones, especially vertical or transverse positions relative to the antero-posterior one.

The purpose of the present invention is to provide an apparatus of the type described at the beginning, that overcomes the drawbacks of the present passive apparatuses by actively supplying an action of guided displacement of the mandibular jaw relative to the maxillary one, while maintaining the construction and convenience advantages of the known apparatuses.

The invention has the further purpose to permit not only action of forward displacement of the mandibular jaw relative to the maxillary one, but on the contrary, also actions of displacement of the maxillary jaw relative to the mandibular one, supplying an action of distraction on the natural maxillary sutures (lines of junction).

SUMMARY OF THE INVENTION

The invention achieves the above-mentioned purposes with a device of the type described at the beginning, in which the two elements are configured such that from the above-mentioned intermediate closure position of the jaws the two elements come into reciprocal contact and slide relatively to each other, thereby exerting together and automatically a push in a direction of relative displacement between the maxillary and the mandibular jaws for the assuming of the correct relative position between the maxillary and the mandibular jaws by the forward displacement of one of them over the other, or vice-versa.

The two guiding elements can be affixed to the dental arches by any type of anchoring elements.

Advantageously, the maxillary jaw and the mandibular jaw are provided with a pair of elements placed on the opposite sides of the antero-posterior axis.

These elements may be mounted on apparatuses of the removable type or on fasteners of the permanent type affixed to the dental arches.

The pair of guiding elements of the maxillary and mandibular jaws, together with their fasteners, may be part of a common supporting and application structure. For example, the fasteners may be connected by means of structures using wires or the like.

The anchorings may be placed directly on one or more teeth of the corresponding arch, either in the form of annular bands that surround the tooth, or in the form of fasteners glued to one or more teeth. Alternatively, the anchorings may be in the form of structures of a type similar to that of removable orthodontic apparatuses. The structural elements that connect the fasteners together may be wires or the like, which are welded to the fasteners or affixed to the same in a movable manner, e.g., by means of thin iron wires or elastics. The structures further may comprise combinations of these fasteners.

According to a variant, said structures may also incorporate other types of operative units for orthodontics, which together with the action of the apparatus object of the invention, provide other corrective functions. For example, the structure may be constructed to provide a divaricating action in a direction transverse to the antero-posterior axis, displacements of the teeth, or other. The structure may also be designed to absorb or in some way regulate or generate forces in a vertical direction, that otherwise the apparatus according to the invention is not capable of generating.

Obviously the two elements associated with the mandibular and with the maxillary jaws, and their relative anchoring elements, can be completely disconnected between them.

According to a further advantageous improvement, the guiding elements may be mounted in a fixed manner, or they may be adjustable in relative position at least in one direction, especially in the antero-posterior direction, and blockable (or lockable) in that position.

These further improvements result from said elements being mounted on sliding guides engaged on the guides connected to the anchoring elements, there being provided limiting stops displaceable and blockable in position, in a movable manner at least in one of the two sliding directions.

It is also possible to provide for elastic means that are inserted between stop or collision points (that are fixed or adjustable in position) and these guiding elements. The elastic means maintain the guiding elements in position with a certain elastic giving force. In this case, the displacement action is further dampened by the yielding quality of the elastic element, relative to a stable but regulatable positioning of the guiding elements.

A further characteristic of the invention is that, in combination with the guiding element, it is possible to provide for elastic elements that resist the closure action of the mandibular jaw against the maxillary jaw (i.e., that act in a direction opposed to this closure displacement). These elastic elements that resist closure action of the jaws are constituted by springs associated with the mandibular jaw and/or with the maxillary jaw and of the stop elements associated with the maxillary or mandibular jaws. Also in the case of these elastic elements that resist the closure of the maxillary jaw against the mandibular jaw, the elements associated with the maxillary jaw and those associated with the mandibular jaw are initially not in engagement with one another; and they enter into action only at a certain point of the closure function. Similarly to the guiding elements, these elastic elements that oppose or resist the closure of the mandibular jaw against the maxillary jaw are arranged in a laterally offset position relative to the teeth of the corresponding arch. These elements have the function of supplying simultaneous moments (i.e., forces) in a direction perpendicular or transverse to the occlusion plane of the dental arches, on the individual dental elements and/or on the bone bases. Such intrusion movements may be necessary to correct errors in placement in the closure position of the two dental arches.

Even though the apparatus according to the invention has heretofore been described with reference to corrective displacements in a direction of the anteroposterior axis, it is obvious that with relatively simple modifications, it is also possible to apply the same construction and the same principle to make corrections in a direction transverse to the antero-posterior axis.

With reference to the above description and especially to the fact that at least one of the two cooperating guiding means associated with the mandibular and maxillary jaws is adjustable with respect to the relative positioning of the two guiding means, it is possible not only to obtain a correction in the antero-posterior direction, but also a correction in the angular direction relative to an axis perpendicular to the antero-posterior direction. In fact, by regulating the position of the guiding means on the two sides of the central antero-posterior axis in a non-symmetrical manner, the mandibular jaw will be subjected to displacements that are different on one side relative to the other side, thus obtaining also a certain rotation of the same and therefore a certain correction of at least one component transverse to the antero-posterior direction.

The guiding elements according to the invention do not generate any force component in the vertical direction, that is to say in a direction transverse to the occlusion axis. Such action may be exerted by integration or combination structures provided to that end in combination with the present guiding elements.

Further improvements of the invention constitute the object of the dependent claims.

BRIEF DESCRIPTION OF THE DRAWINGS

The characteristics of the invention and the advantages deriving from them will be better understood from the following description of a few examples of execution, that are non-limiting and are illustrated in the attached drawings in which.

DETAILED DESCRIPTION OF THE PREFERRED EMBODIMENTS

With reference to FIGS. 1 to 11, the apparatuses illustrated therein have the function of displacing forwardly the mandibular jaw 3 relative to the maxillary jaw 4. Persons skilled in the art will thus recognize that the apparatuses illustrated in these figures are oriented to best correct a Class II malocclusion (i.e., an overbite).

The apparatuses according to the remaining FIGS. 12 to 18, by contrast, have the function of supplying a displacement of the maxillary jaw 4 with respect to the mandibular jaw 3. These apparatuses are substantially characterized by a symmetrical reversal of the orientation of the guiding means 1, 2 shown in the apparatuses of FIGS. 1 to 11. The displacement of the maxillary jaw in FIGS. 12 to 18 is mostly due to a distraction effect of the maxillary sutures. Persons skilled in the art will recognize that this condition is known as a Class III malocclusion (i.e., an underbite).

It is understood that the different embodiments illustrated herein may be combined among themselves with respect to some construction characteristics illustrated as limited to specific embodiments, but that may be also adopted in others of the illustrated embodiments.

In FIGS. 1 to 5 there is illustrated a first embodiment of the apparatus according to the invention. The apparatus according to the invention comprises two pairs of guiding elements 1, 2, cooperating with each other but not connected to each other. The guiding elements 1, 2 of each pair are configured to be affixed to the corresponding dental arch of the mandibular jaw 3 and of the maxillary jaw 4 in a substantially symmetrical position relative to the median antero-posterior axis. The guiding elements 1, 2 of each pair, one of which is associated with the mandibular jaw and the other one with the maxillary jaw, are fixed onto the corresponding dental arch in a coinciding position so as to cooperate with each other during the closure of the mandibular jaw against the maxillary jaw. The two guiding elements 1 and the two guiding elements 2 associated with the mandibular jaw 3 and with the maxillary jaw 4, respectively, are substantially the same but not necessarily identical. For brevity, the construction description will refer only to the elements of one of these two pairs of guiding elements.

Figure 1:
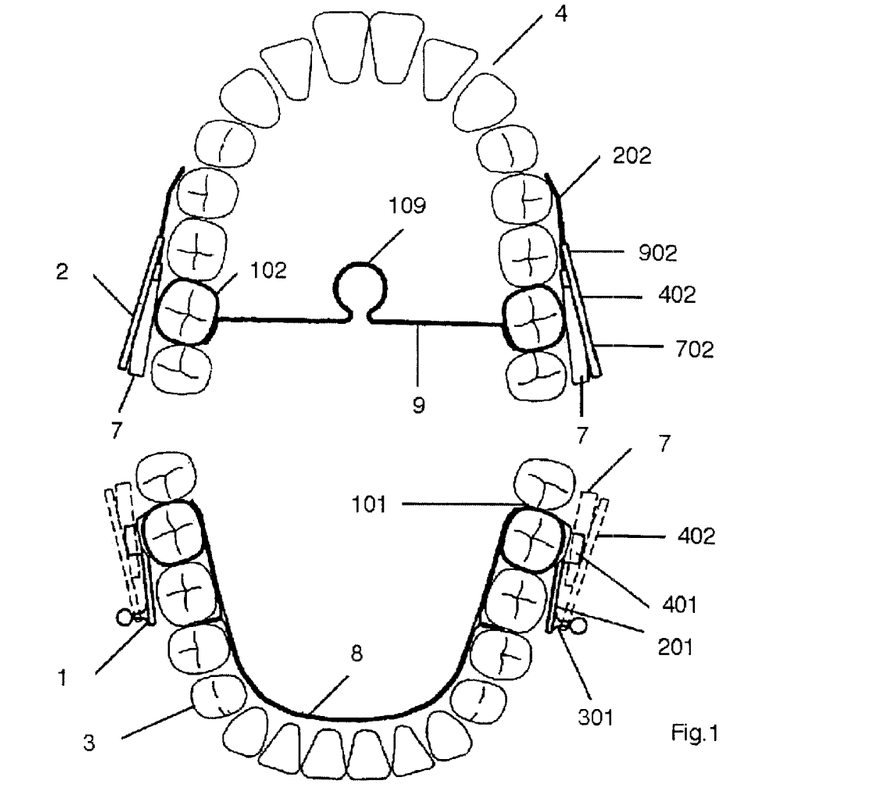
FIG. 1 illustrates a plan view of the dental arches of the maxillary and of the mandibular jaws to which an apparatus according to a first embodiment of the invention has been applied.
Figure 2:
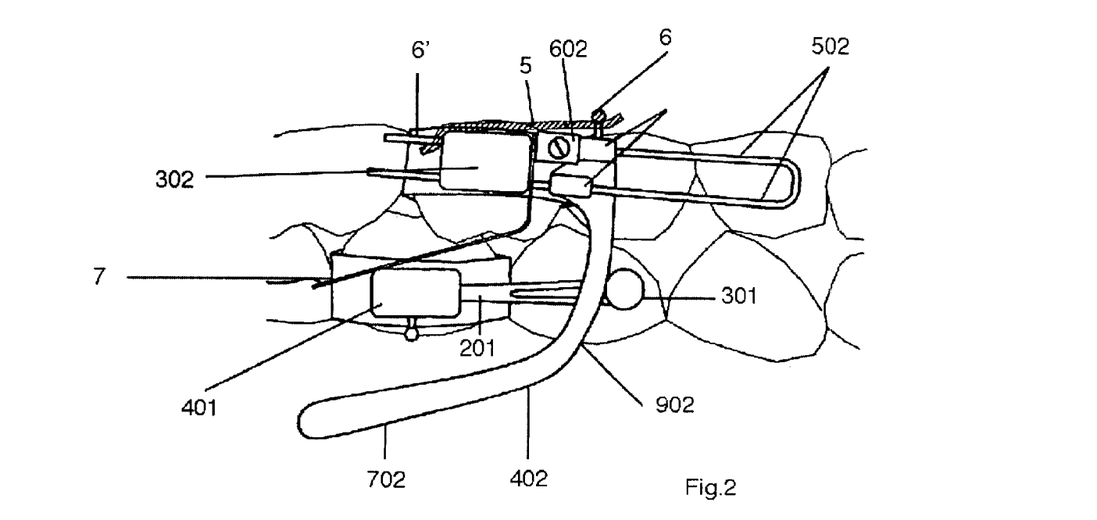
FIG. 2 illustrates an enlarged lateral view of a detail according to the invention.

The guiding element 1 is affixed to a tooth of the mandibular jaw 3 by means of an anchoring band 101 that encircles this tooth. On the external side of the dental arch, toward the cheek, there is welded or soldered to the anchoring band an arm 201 that is oriented in the antero-posterior direction or (in a direction) substantially tangent to said anchoring band 101. At its free end this arm 201 carries, jutting out, a transverse stop element 301 that projects toward the cheek and that has a rounded head so as not to bruise the cheek itself. The extension of the stop element 301 is substantially perpendicular or even transverse to the antero-posterior axis, and it advantageously has a cylindrical or even a rounded section. Advantageously, in axial section, the transverse extension of the stopping element 301 has a concavity resulting from its being executed with a smaller diameter in its median zone. In the connection zone of the arm 201 with the band 101 for anchoring it to the tooth, on the external side of this band, there projects, in an overhanging manner, an abutment surface 401 substantially co-planar with the subtending plane of the dental arch. The projections of the transverse stop element 301 and of the abutment surface 401 are such that they do not cause any disturbance to the cheek.

The guiding element 2 associated with the maxillary jaw 4 also comprises a band 102 for anchoring it to a tooth of the dental arch of the maxillary jaw. The guiding element 2 has a sliding guide, especially a pair of sliding guides 202, in a position external to the dental arch. More particularly, the pair of sliding guides 202 are in a position similar to that of arm 201 in guiding element 1, that is, in the direction antero-posterior or tangent to the dental arch, and also in a position parallel to the subtending plane of that arch. The pair of sliding guides 202 may be fixed in any manner to the anchoring band 102, and in the particular embodiment illustrated, are engaged in a small tightening fixation block (or lock) 302 formed as one piece with the anchoring band 102. Obviously these two guides 202 may also be mounted in a tightening fastener of the removable type, for example by means of tightening screws or the like or fixed by any other fastening means commonly used, especially in orthodontics apparatuses.

On the guides 202 there is fixed a cam element 402 that can slide along them due to a slide 502 affixed to one end of this cam 402. The slide 502 is made up of a pair of tubular elements slidingly engaged each one on one of the two guiding shafts of the double guide 202. The cam 402 is constituted by an angled peg or pin that extends substantially in the direction of the closure of the mandibular jaw toward the maxillary jaw beyond the occlusion plane. The cam element 402 has two terminal portions 702, 802 oriented perpendicularly or transversely to each other. One end portion 702 of the cam element, at the free end thereof, is substantially parallel to the occlusion plane. The other end portion 802 of the cam element, at the fixation end to the slide 502, is substantially oriented perpendicularly to the occlusion plane, but in a direction substantially tangent to the direction of closure of the mandibular jaw against the maxillary jaw. The two sections 702, 802 are connected by an arched connection part 902 that is molded in such manner that the extrados surface (i.e., outer curved surface) progressively comes to the level of the corresponding anterior side of the portion 802 with reference to the antero-posterior position of this portion.

A stop element 602, which is displaceable and movably blockable (or lockable) in position, is provided on one at least of the two guiding pins of the double guide 202. The displaceable stop element 602 is, for example, constructed as a small ring slidingly engaged on one guiding pin of the double guide 202 and blockable in position by means of a radial tightening set screw. Obviously, it is possible to provide for a small ring on the other guiding pin also, with the two small rings being separate or connected. The displaceable stop element 602 is provided on the posterior side of the slide 502. On the opposite side of the slide 502, that is on its anterior side, no stop element is provided even though it is possible to have one and can safely be provided.

In the embodiment illustrated, however, the stop element is provided only on the posterior side of the slide 502, while the cam element 402 is held against displacement in the anterior direction by an elastic element 5. For example, an elastic element of rubber or other suitable material is hooked to hooking projections 6, 6' (which may for example be formed one piece with the slide 502) and to the anchoring band 102.

In a position lined up relative to a plane perpendicular to the occlusion plane, and in a position posterior to the cam pin 402, the anchoring band 102 of the guiding element 2 carries an elastic element 7 that is meant to cooperate with the abutment surface 401 of the guiding element 1. Advantageously, the elastic element 7 is constituted by a leaf spring that is formed of a small elastic tongue projecting in a slanted direction from the occlusion plane of the dental arch associated with the maxillary jaw 4 toward the mandibular jaw 3 and in a position coinciding with the abutment surface 401. The cam pin 402, on the other hand, is meant to cooperate with the transverse extension of the stop element 301, especially its extrados side, that is to say its anterior side. More specifically, the cam pin 402 is meant to abut, first with its part 902 that connects the two terminal portions 702, 802, against the anterior side of the transverse stop element extension 301, becoming engaged in the peripheral recess or groove on the opposite posterior side of the same. That is, cam pin 402 becomes comes into contact with transverse extension 301 beginning from a pre-set intermediate closure position of the mandibular jaw 3 against the maxillary jaw 4. The cam element 402, and especially the arched connection portion 902, are constructed so that the extrados surface (or the anterior side) of the cam element 402 assumes the correct position with respect to the transverse extension of the stop element 301, and lined up with same, during closure of the jaws.

Figure 3:
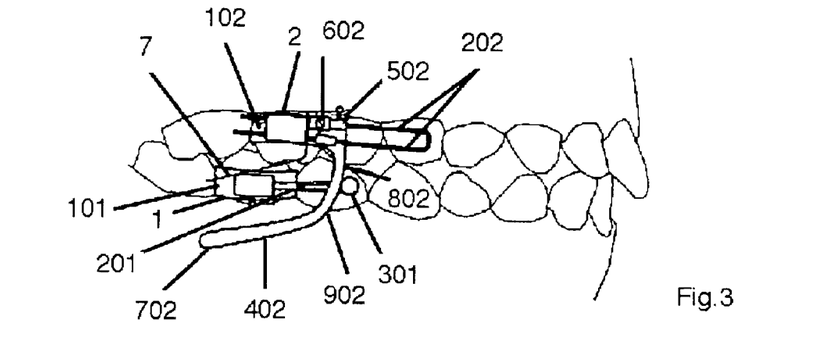
FIGS. 3 to 5 illustrate a few operational phases of the apparatus according to the invention shown in FIGS. 1 and 2.
Figure 4:
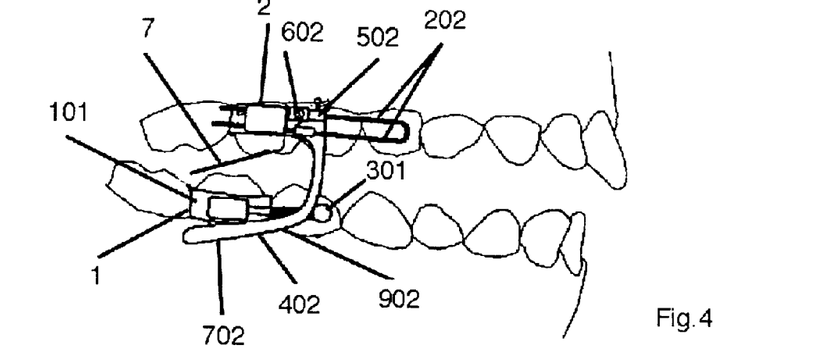
Figure 5:
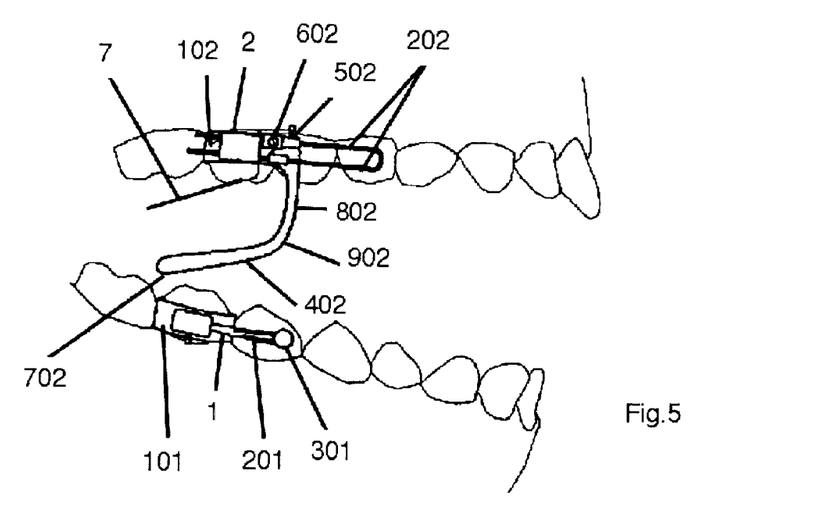

As illustrated in FIGS. 3 to 5, initially the two guiding elements, and especially the cam element 402 and the transverse extension of the stop element 301, are not in contact with each other. Under conditions of partial forward displacement of the mandibular jaw 3 toward the maxillary jaw 4 or of appreciable partial closure, however, the cam element 402 comes in contact with the transverse extension of the stop element 301 with its rounded part, that is to say with the intermediate part of the arched connection 902. During the further closure movement, due to the molding of the portion of the arched connection 902 that runs (or slides) over the transverse extension of the stop element 301, there is automatically exerted a progressive action of displacement of the mandibular jaw in the antero-posterior direction, and in this case a forward one. That is, the progressive corrective action occurs automatically, without the patient having to exert any action left to his discretion and caused by any hindrance to the execution of the displacement movement of the mandibular jaw as a whole, and with the sole effort of a simple movement of the mandibular jaw. In this manner the patient performs the correction, by executing only movements instinctively known to him, and without having to execute any forced movement that requires a willful and unusual act on his part.

Figure 5A:
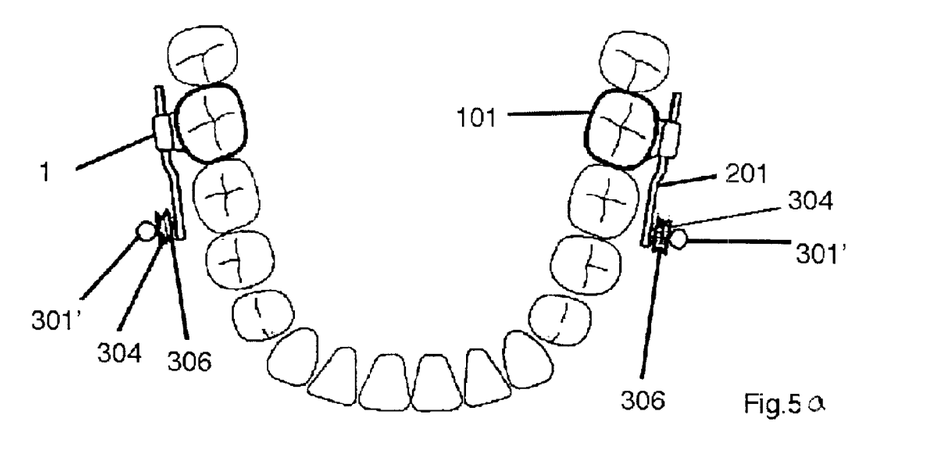
FIG. 5A illustrates a plan view of the dental arch of the mandibular jaw to which a portion of an apparatus according to a further embodiment of the invention has been applied.

According to an improvement illustrated in FIG. 5A, easily constructed by the technician in the field, the transverse extension of a stop element 301' of the guiding element 1 may be constituted by a simple shaft on which there is mounted a rotating small roller 304. This small roller 304 advantageously has a median groove 306 coaxial with the engagement of the cam element 402 that serves as a guide by limiting transverse displacements of the cam element 402 similarly to the groove of the illustrated transverse stationary stop element 301. Thus, during closure movement of the mandibular jaw 3 and maxillary jaw 4, the small roller 304 functions to guide element 402 and also decrease friction between the cam element 402 and the stop 301', which thereby facilitates a smoother and more natural closing action. The small roller 304 may be made from any suitable material, including a metal such as steel, stainless steel, titanium, and the like. Advantageously, roller guide 304 may also be from a plastic or elastomeric material such as medical grade polyurethane, or any other material that provides a further cushioning and force dissipation when desirable.

Returning now to FIGS. 3 to 5, at a certain point of the closure displacement of the mandibular jaw 3 against the maxillary jaw 4, the small slanted elastic tongue 7 comes to hit against the abutment surface 401. This action, which occurs simultaneously with the action of antero-posterior displacement of the mandibular jaw 3, exerts a force that opposes (or resists) the closure movement of the mandibular jaw 3. This makes it possible to execute an accompanying gymnastic that strengthens the muscles that take part in the mastication activity. The small elastic tongue 7, as well as the cam element 402, project outside of the dental arch to a very limited extent, and thus fit within the oral cavity without any difficulty. Furthermore, the free end portion 702 of the cam element 402 is folded in a position such as to be transverse to the direction of movement of the mandibular jaw 3. As a result, it does not cause any unpleasant scratching or other action on the walls of the cheek or of the mouth.

The slide 502 mounted on the guide 202 makes it possible to accurately regulate the corrective forces causing forward movement of the mandibular jaw 3, exerted by the two guiding elements 1, 2. Furthermore, such an action can easily be progressively increased, thus rendering the patient used to the correct position of the jaws in successive steps of increasing displacement. This prevents a sudden traumatic action relative to the position habits set by the patient, which may be troublesome and also painful at least at the beginning. The regulating is simple and rapid.

A further advantage of the present embodiment is that it is possible to regulate in a differentiated manner the displacement actions exerted on the two sides of the mandibular jaw, with reference to the median axis. This can be accomplished by regulating in a different manner the position of the two elements of the cam 402. In this way, in addition to a simple displacement in the antero-posterior direction, it is possible to execute also an action of angular displacement and/or an action on at least one transverse component of the antero-posterior axis.

Obviously, even though in the present example the transverse extension of the stop element 301 is stationary relative to its antero-posterior position, it is possible to mount it on guides in the same manner as the cam element 402. This is possible either as an alternative to the mounting on guides 202 of the cam element 402 that in this case is fixed, or in combination with an assembling adjustable in position also on the guides of the cam element 402.

Even though in the preferred embodiments of FIGS. 1 to 5, the cam element 402 in the form of a molded or arched pin is fixed to one tooth of the maxillary jaw while the cooperating transverse extension of the stop element 301 is carried by a tooth of the mandibular arch, it is also possible to provide for the reverse arrangement of the two guiding elements 1 and 2.

The guiding elements 1 and 2, respectively associated with the mandibular jaw 3 and with the maxillary jaw 4, can be separate from each other as well as joined by means of a carrying structure. Such carrying structure may serve only as simple connection and joining means, or it may assume functions of distribution of the forces exerted on the mandibular jaw 3 and on the maxillary jaw 4 as well as on other anatomical parts, in order to relieve the pull on the individual teeth, thus preventing effects of displacement of the teeth themselves.

The above structures may have any configuration, such as configurations known in orthodontics. In the case of the example according to FIGS. 1 to 5, the anchoring bands 102 connected to the teeth of the maxillary jaw and the anchoring bands 101 connected to the teeth of the mandibular jaw are connected by transverse elements, such as wires or the like, indicated by 8 and 9 (see FIG. 1). More especially, the two anchoring bands 101 of the guiding elements 1 associated with the mandibular jaw 3 are connected among themselves by an arched wire 8 that is fixed—either movably by means of engagement elements or simply by a welding or soldering—with its ends to the anchoring bands 101 themselves. The connection wire 8 is constructed as an arch extending along the internal side along the dental arch from one to the opposite of the anchoring bands' faces 101 of the guiding elements 1.

The anchoring bands 102 of the guiding elements 2 associated with the maxillary jaw are connected among themselves by an element, especially a transverse wire 9. Transverse wire 9 extends in an arched form along the palate and, in its median zone, may present a support element 109 extending to the palate. This element 109 serves to increase the surface of support on the palate, rendering the wire 9 relatively elastically adaptable axially as well as radially toward the palate. To the elements 8, 9, or to other similar ones, there may be associated other functional means that together are constructed to execute operations of orthodontics. For example, spreading elements made up of two elements interconnected in a reciprocally displaceable manner to move closer and farther away from each other, or other known functional elements, may be associated with elements 8, 9.

Figure 6:
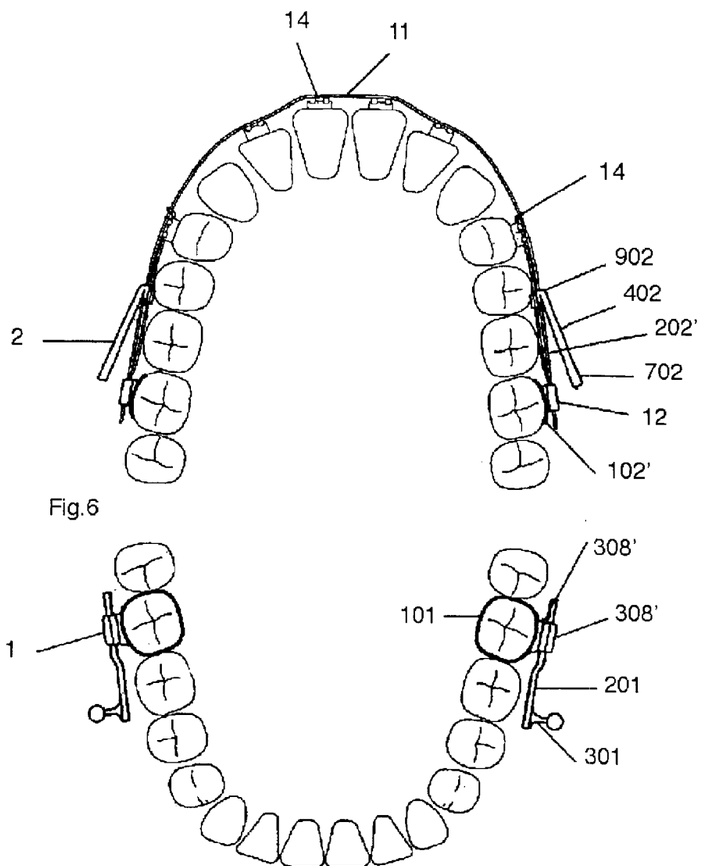
FIG. 6 illustrates a view similar to that in FIG. 1, of an alternative embodiment of the invention.
Figure 7:
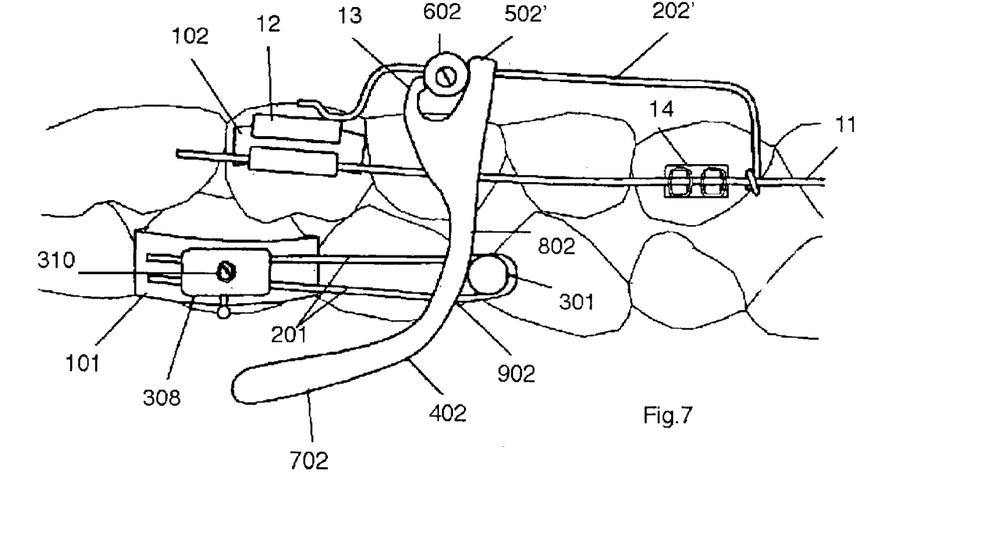
FIG. 7 illustrates a lateral view of an enlarged detail of the apparatus according to FIG. 6.

The FIGS. 6 and 7 illustrate an alternative embodiment of the example illustrated in FIGS. 1 to 5. In this case, however, the guiding elements 1 associated with the mandibular jaw 3 show a construction substantially similar to that of the preceding figures. The sole variations consist as follows. The arm 201 that carries the transverse guiding extension 301 is made in the form of a wire folded (or bent) on itself. In the fold (or bend) zone, the guiding element 301 carries the transverse extension of the stop element 301. The two free ends of the folded wire element 301 are affixed to the anchoring band 101 by means of a tightening element 308 similar to tightening element 302 provided for the guides 202 of the guiding element 2 of the preceding example. This construction permits regulating of the position of the extension of the transverse stop element 301 relative to the antero-posterior direction. If the tightening element 308 is then made with removable or releasable tightening elements, such as by splitting element 308 into two sections 308', 308' and clamping them together with a screw 310, the arm 201 can then slide forward or backward. This arrangement permits a certain regulating of the position of the transverse extension of the stop element 301.

With respect, on the contrary to the guiding elements 2 associated with the maxillary jaw 4, the anchoring to the tooth is done by means of a fastener 102' glued to the support tooth. In this example, the guide 202' is a single one, as is the slide 502', which is constituted by an elastic and arched element that leaves from a support wire 11 in an anterior advanced position relative to the support tooth and to the anchoring 102'. The opposite end of the guide 202' is molded in such manner that it can be elastically engaged in a coupling seat 12 coming as one piece with anchoring 102'. The slide 502' further has a posterior appendage 13 that is meant to engage in a springy manner behind a spring-type groove surface constituted by the same adjustable posterior stop element 602. More especially, the stop element 602 has a convex arched surface turned toward the spring-like engagement means which forms an inviting surface for its elastic engagement coupling with the appendage 13. The stop element 602 is also executed rounded and provided at a pre-set distance from the posterior side of the slide 502' that collides against this adjustable stop element 602. Such distance is opportunely measured to permit the appendage to be elastically forced against the posterior ascending portion of the arched engagement surface, thus elastically tightening the adjustable stop element 602 between the posterior side of the slide 502' and this spring engaging appendage 13. Advantageously the adjustable stop element 602 is made with a substantially round section, for example a cylindrical one, and it has a radial perforation for the passage of the pin of guide 202', and a threaded axial perforation for a bolt that blocks (or locks) it into position.

The cam element 402 is executed substantially identical to that of the preceding example. In this construction, however, there is also possible an easy substitution, in the assembled condition, of the elements of guide 2 of the cam element 402. That is, the cam element 402 is easily moved along guide 202' or removed from the apparatus. This makes it possible to regulate not only its position with reference to the antero-posterior axis but also to mount different cam elements 402. In the present example the guiding elements 1 associated with the mandibular jaw are independent from one another. By contrast, the elements of guide 2 associated with the maxillary jaw are connected by a structure that is constituted by the wire 11 to which there is joined the anterior end of the pin of the arched guide 202'. This wire 11 extends from one to the other of the two anchorings 102', running along the external side only of the dental arch and supported by, and affixed to, one or more teeth along its extension by means of anchorings 14. The latter are typical for these wire structures and are glued to the teeth.

Figure 8:
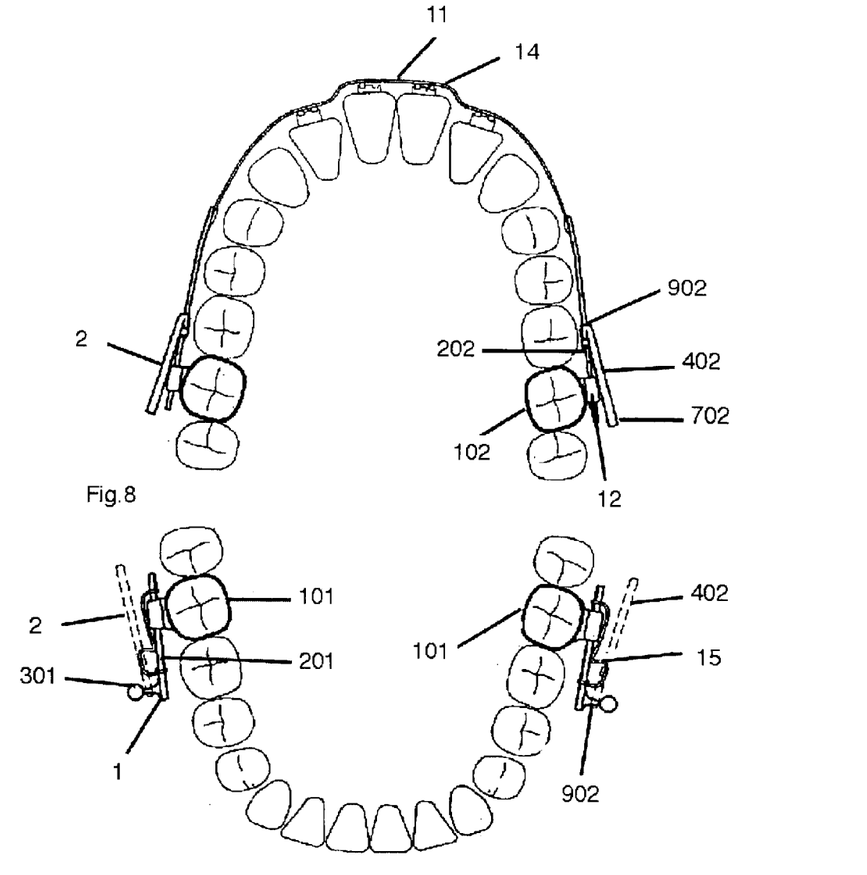
FIG. 8 illustrates, in a manner similar to FIGS. 1 and 6, a further embodiment of the invention.
Figure 9:
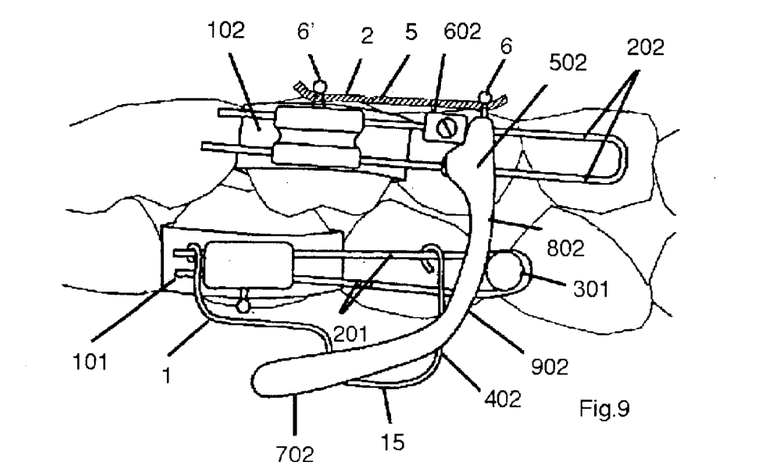
FIG. 9 illustrates a view similar to those in FIGS. 2 and 7, for the apparatus according to FIG. 8.

FIGS. 8 and 9 illustrate a further variant with respect to those of the preceding figures. In these variants, a different structure and positioning of the elastic element 5 supports the cam element 402 and its related slide 502 against the adjustable stop element 602. In addition, the arm 201 (which is executed in a manner similar to the example in FIGS. 6 and 7 by a wire bent on itself in the manner of a fork) has a further stiffening wire 15 that is hooked or fixed between the posterior end of one of the two branches. Strengthening wire 15 includes a first intermediate portion between the fixation and tightening elements of one of the two branches, and a second intermediate portion between the tightening fixation elements of said posterior end and the transverse extension of the stop element 301. This strengthening wire 15 may be molded in such manner as to exert a variable force during stress, being at least within elastically deformable limits in the manner of a tie (or tension) rod.

Figure 9A:
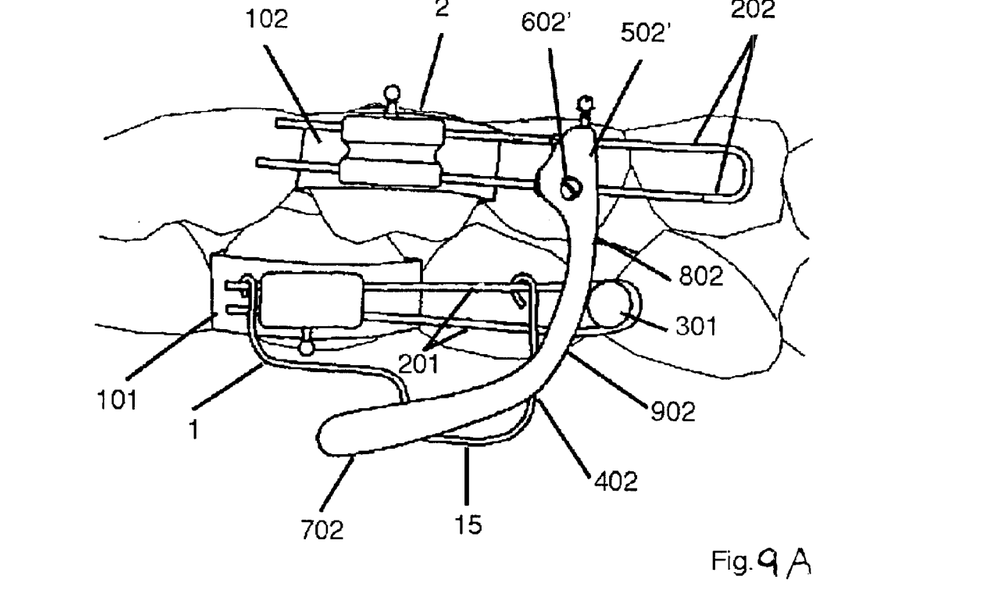
FIG. 9A illustrates, in a manner similar to FIG. 9, a further embodiment of the invention.

FIG. 9A illustrates a further variant with respect to those of the preceding figures that is similar in most respect to the embodiment in FIG. 9. The primary difference is that the slide 502' includes an integrally formed stop element. For example, a set screw 602' may be engaged in a threaded aperture formed in slide 502'. Advantageously, this arrangement eliminates the need for the elastic element 5 the separate stop element 602 (see FIG. 9). Although the apparatus of FIG. 7 also did not require the elastic element 5, this arrangement differs from the one of FIG. 7 in that it further does not require the separate stop element 602. Thus, manufacture of the apparatus is simplified compared to the device in FIG. 7. Assembly and adjustment of the device in the patient's mouth is also simplified.

Figure 10:
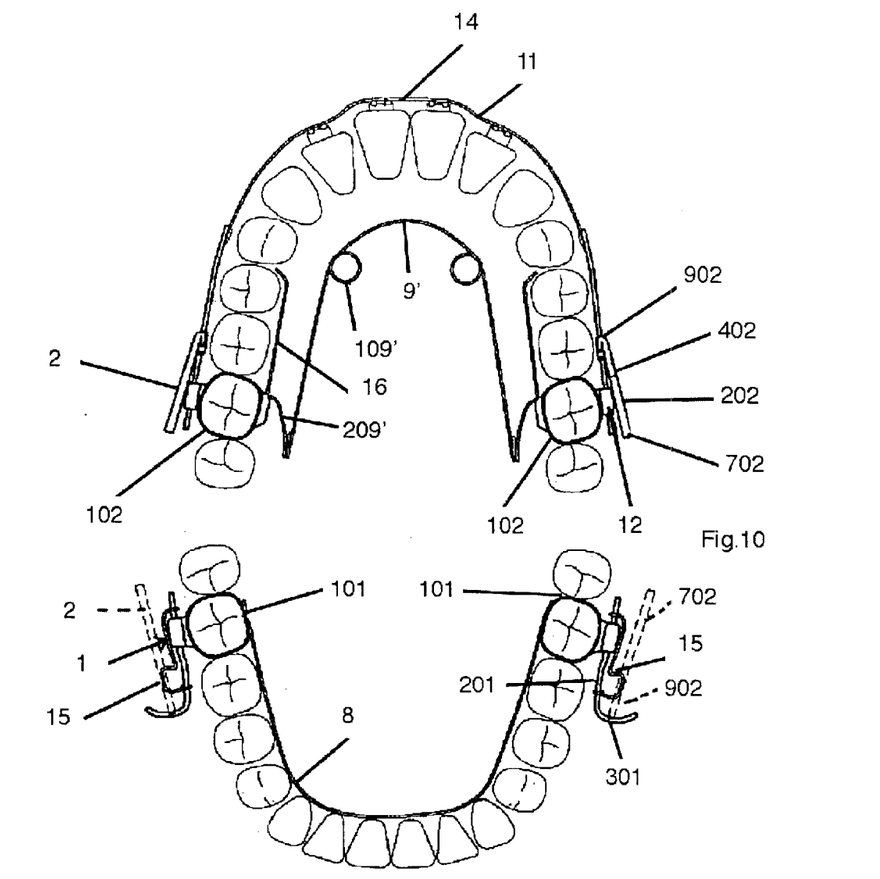
FIGS. 10 and 11 illustrate views similar to those in FIGS. 1 and 2, of a further embodiment of the invention.
Figure 11:
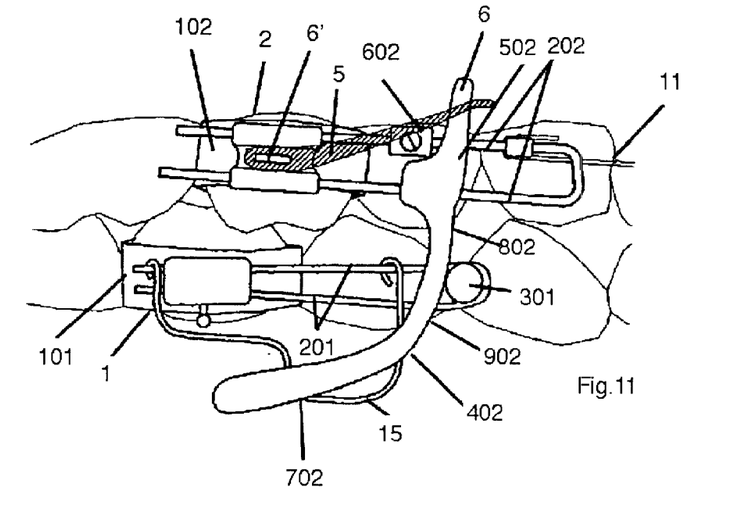

The example in FIGS. 10 and 11 is appreciably derived from that in FIGS. 8 and 9. It deviates from that of the preceding figures by the different position of the hooks 6, 6' of the recall elastic 7. Furthermore, the anchoring bands 101 to the teeth of the mandibular jaw 3 are connected among themselves by a wire 8, similarly to the example in FIGS. 1 to 5. The guiding devices 2 associated with the maxillary jaw are also connected among themselves. This is done with a wire 11 that is similar to the one in examples of FIGS. 6 and 8, however, the wire 11 is fixed not to the anchoring elements 102 to the teeth of the maxillary jaw 4, but rather to the anterior end of a guiding pin of the double guide 202 through the slide 502. Furthermore, the anchorings 102 (of the bands type) are internally connected among themselves by an internal arc 9'. The function of the arc 9' is to decrease the stress on the palate in an internal band that runs along the dental arch. This arc 9' has widening and elasticizing rings or spires 109', and it is connected in a springy manner to the anchorings 102 by means of the support wires 209'. A further support is constituted by a wire 16 that extends at the base of the dental arch, partially along the same.

Figure 12:
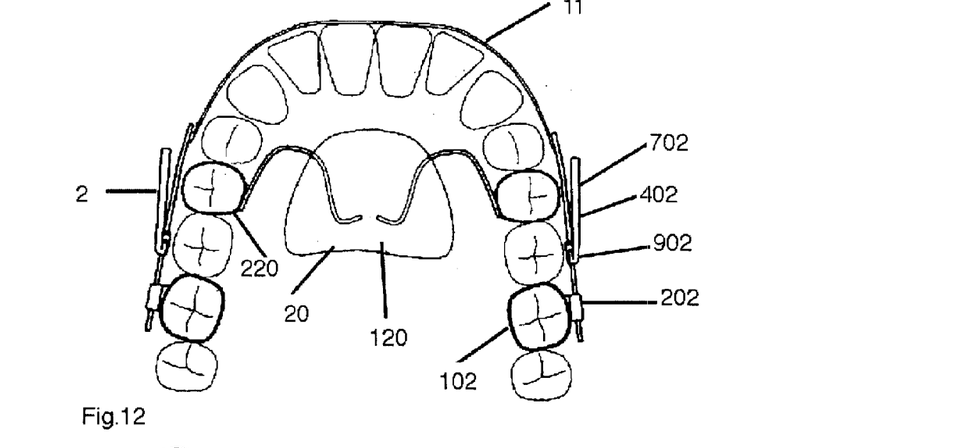
FIGS. 12 and 13 illustrate, similarly to FIGS. 1 and 2, an alternative embodiment of the invention, that is capable of exerting a corrective action in a direction opposite the one in the embodiments of FIGS. 1 to 11.
Figure 13:
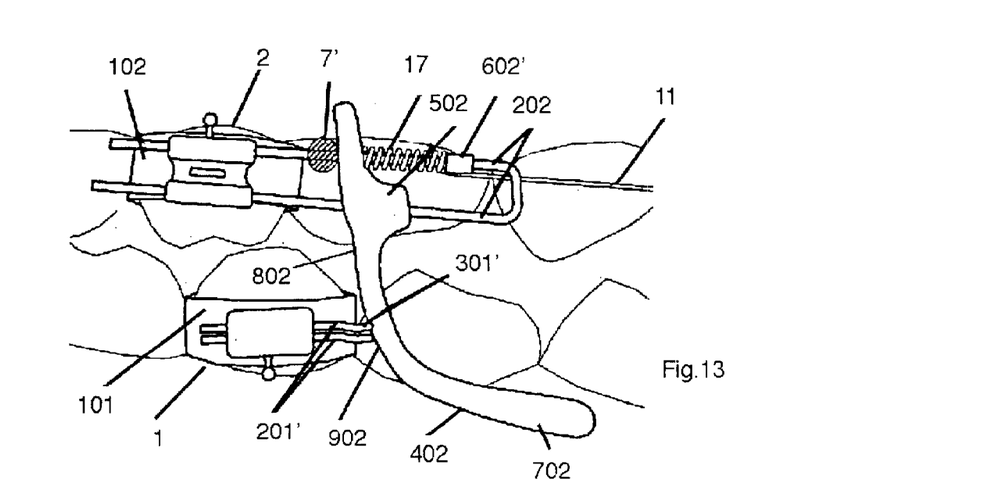

The FIGS. 12 and 13 illustrate another embodiment of the apparatus according to the invention. This embodiment is meant to exert an antero-posterior action of displacement of the maxillary jaw in the forward antero-posterior direction, that is, in the opposite direction (relative to the apparatuses of the preceding figures) on the mandibular jaw. The main difference is that the cam element 402 is placed in a reversed manner with respect to that of the preceding figures, that is, with its active surface turned backward and with its terminal portion 702 turned forward. Furthermore, this cam element 402 cooperates with the opposite side of the transverse extension of stop element 301'.

With reference to the example according to FIGS. 12 and 13, there are illustrated other variants in construction of the guiding elements 1, 2 that must be understood as not limited only to that example of execution. Instead, they are indeed also applicable with reference to the preceding examples of execution with the favorable and obvious modifications dictated by the different displacement direction of the mandibular jaw that must be obtained. Similarly, the specific construction characteristics of the preceding examples are applicable, and are understood to be so, also to the present example according to FIGS. 12 and 13, with the obvious and favorable modifications. With respect to the guiding element 1, the arm 201' and its transverse extension 301' are constituted by a double wire with one end made fixed, especially by means of an element to be tightened to the anchoring element 101 to the tooth. The other free end of the double wire projects in an over-hanging manner and is suitably molded so as to form a transverse collision extension with a recessed lodging in the active surface of the cam element 402. Obviously, the wire may also be molded so as to form an axis of rotation for the support of a small running roller, grooved as described with reference to the example in FIGS. 1 to 5. The cam element 402, the shape of which is symmetrically similar to that of the FIGS. 10 and 11, is in this case mounted elastically yielding in the opposite direction relative to the direction of the correction push that is to be exerted. To that end, between the stop element 602' that in the present example is fixed, but that may also be adjustable, and a collision surface of the slide 502, there is inserted a spring 17. Spring 17 is preferably a spiral spring threaded over the pin of the guide 202. The means for maintaining the slide 502 in position to prevent displacement in a direction of the push are fixed in this case and constituted by a radial widening on the pin of guide 202. For example, a small closed ring or a small ring similar to that of the adjustable stop elements, could be used. Advantageously, this very weakened form of execution of the guiding element 2 with elastic means 17 yielding in the opposite direction (relative to the direction of the correction), may also be applied to the forms of execution relative to FIGS. 1 to 11.

In this example, the anchoring elements 101 and 102 can be disengaged from each other, or as illustrated, connected by elements of a structure. The guiding elements 1 are connected among themselves by a structure similar to that in FIGS. 1 and 10, while the guiding elements 2 are connected by an external wire 11 held in intermediate position by possible engaging elements, as in the structures illustrated in FIGS. 6, 8 and 10. However, in this case there is provided, in combination, a structure for release of the stress indicated as a whole by 20. Structure 20 cooperates with the central zone of the palate by means of a support knob 120, which is affixed to the dental arch of the maxillary jaw 4 by separate anchorings 220 on teeth that are different from those for the anchoring of the guiding elements 2. This type of structure also is applicable to the forms of execution of the preceding examples and vice-versa.

Figure 14:
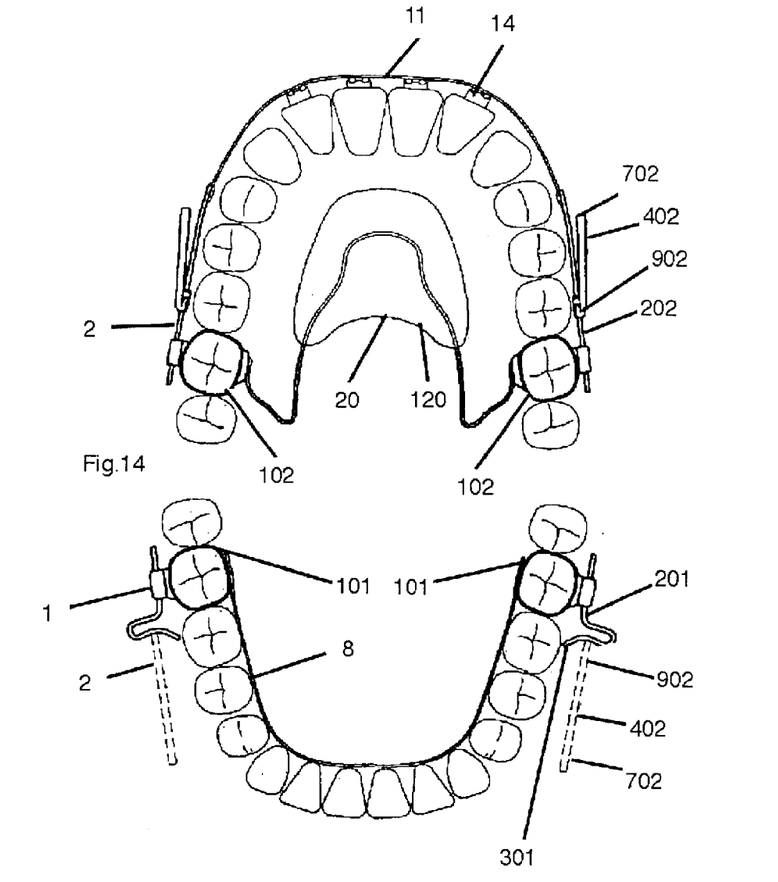
FIGS. 14 and 15 illustrate, similarly to FIGS. 12 and 13, a further embodiment of the apparatus according to FIGS. 12 and 13.
Figure 15:
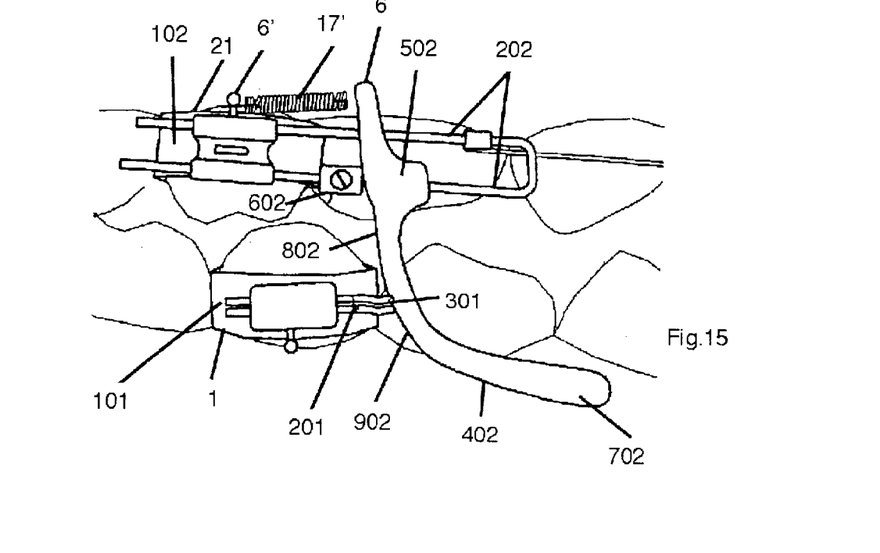

In the variant in FIGS. 14 and 15, the guiding element 1 is identical with that of the preceding example according to FIGS. 12 and 13. However, the guiding element 2 shows an adjustable stop element 602 that prevents the displacement, in direction opposite that of the push, of the slide 502 and of the cam element 402 mounted on it. The weakened support of the cam element is obtained in this case by a spring 17' that works in a direction opposite that of the preceding example. That is, spring 17' works in a direction of tractioning cam element 402 against the transverse extension of stop element 301 of the opposite and cooperating guiding element 1. Said elastic element 17' is in the form of an coil spring. One end of spring 17' is secured to a hook 6 on the cam element 402 or the slide 502, and the other end of spring 17' is secured to a hook 6' formed as one piece with the anchoring element 102. This arrangement is advantageous in that the elastic element 17' with a traction action is hooked to the hooks 6, 6' already provided, and used in the preceding example for the elastic elements 5 that hold the cam element and/or the slide associated with same, against the adjustable stop element 602. The guiding elements 1 and 2 are connected together by a structure 8, 11, 20 completely similar to that of the preceding example except for the fact that the transverse structure 20, for release of the force on the palate, is set on the same anchoring elements 102 as the guiding elements 2.

Figure 16:
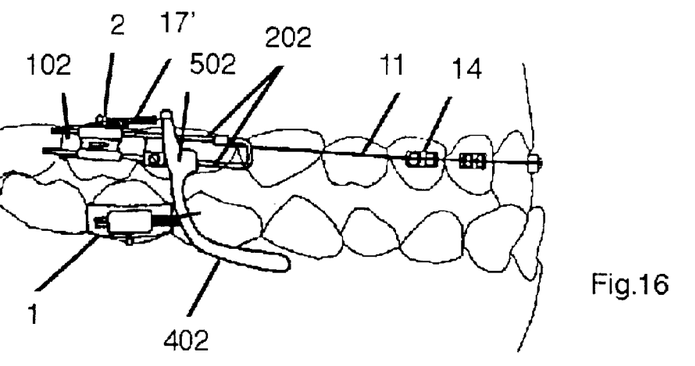
FIGS. 16 to 18 illustrate a few phases of operation of the apparatus according to FIGS. 14 and 15.
Figure 17:
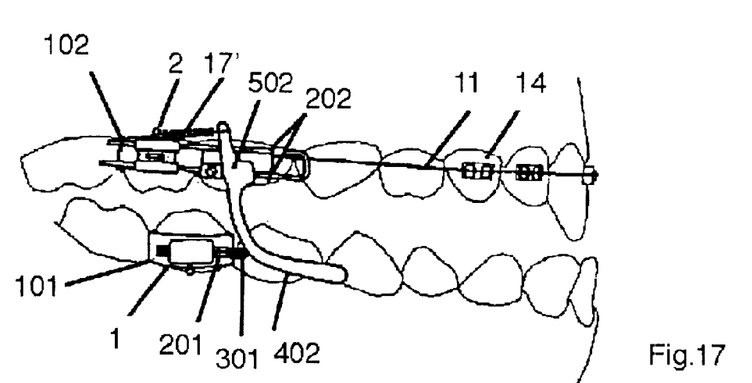
Figure 18:
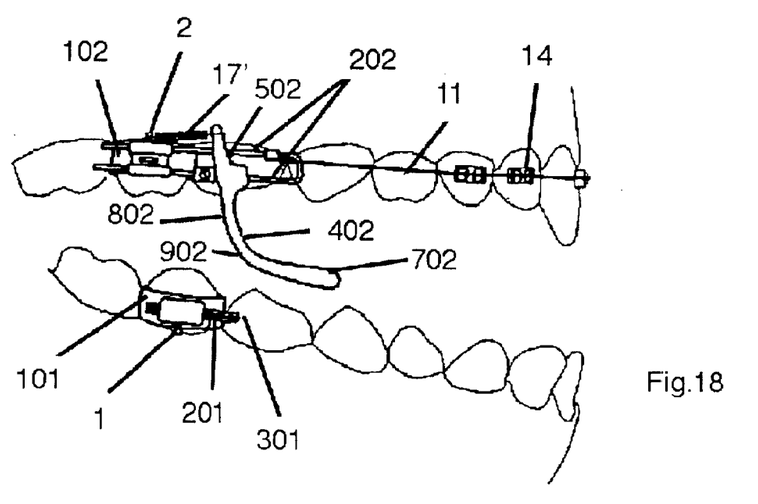

The functioning of the apparatuses according to the forms of execution in FIGS. 12 to 15, is illustrated in a few stages in FIGS. 16 to 18, in a manner similar to those in FIGS. 3 to 5. In this case, the variant illustrated is that of FIGS. 14 and 15, but with the sole substantial functional difference that relates to the traction mode of functioning of the elastic element 17'. The compression type elastic element 17 or traction-type element 17', not only offers an advantage in that the force of correction is applied in forward displacement of the maxillary or of the mandibular jaw—depending on the type of application—in a smoother or softer manner, but it also provides the function of extending the time between two successive adjustments of the position of the guiding element 2. Indeed, with a rigid meeting of the cam-like element 402, when the patient has become used to the correction imposed, the further corrective action is lacking and it is necessary to adjust the position of the cam-like element 402 to re-create the conditions of active push. With the elastic element 17 or 17', however, the corrective action is exerted as long as the elastic element is charged (under tension or compression), and therefore the required adjustments to maintain active the cam element 402 are less frequent.

Figure 19:
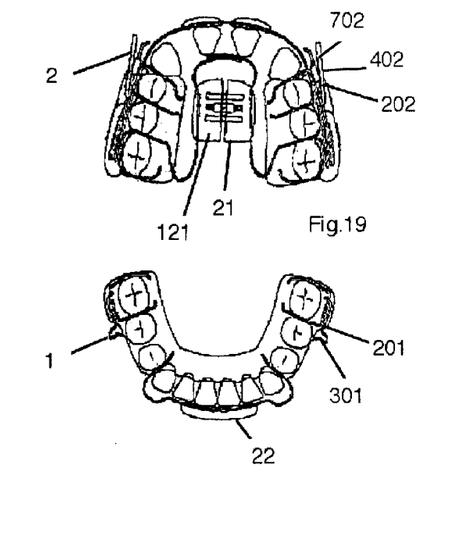
FIGS. 19 to 22 illustrate, similarly to the preceding figures, two examples of embodiments in the form a removable apparatus.
Figure 20:
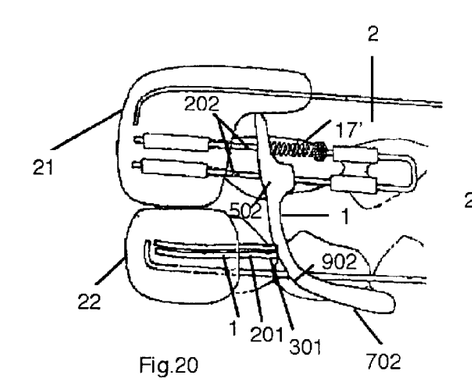

As an alternative to the above, the guiding elements 1, 2 may be arranged on the internal side of the dental arch, even when the latter, especially in the fixed versions of the apparatus, prove to be uncomfortable for the patient as well as for the doctor. The guiding elements may further be supported by apparatus structures of the removable type with a construction similar to that of the removable orthodontic apparatuses. This is illustrated in FIGS. 19 to 22. In one case, illustrated in FIGS. 19 and 20, one of the two apparatus structures 21 and 22 has, in the median zone of the palate, an adjustable spreading element 121 of the type used in orthodontics. This constitutes one example of a combination of the apparatus 1, 2 according to the invention, with another operative unit. The form illustrated in FIGS. 19 and 20 presents an elastic element 17 working in compression on the cam element 402. The transverse stop element 301 is carried by the structure 22.

Figure 21:
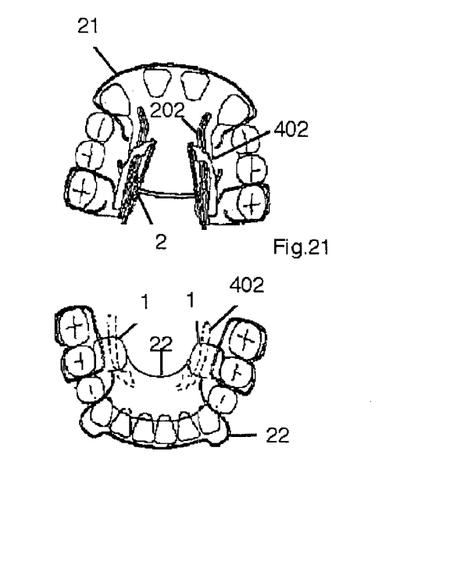
Figure 22:
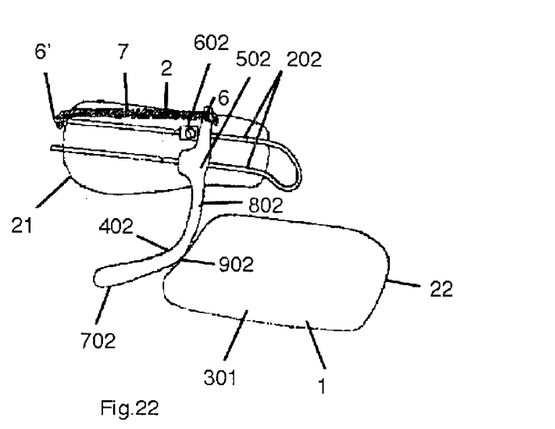

In FIGS. 21 and 22, the two structures 21 and 22 of the removable apparatus carry the guiding elements 2 and 1, respectively, in the internal zone of the corresponding dental arch. In this case the cam element 402 cooperates on the guide 202 with a stop element 602 that is displaceable and blockable in position. The transverse stop element 301 is constituted in this case by an element of the structure 22 suitably molded, especially an inclined plane.

What is claimed is:

1. An apparatus for correcting the relative position between the maxillary and the mandibular jaws in a patient, comprising:

a first pair of guiding elements, the guiding elements being disconnected from each other when the jaws are in an open position and being in cooperating contact between a first pre-set intermediate closure position of the jaws and a complete closure position of the jaws; and means for anchoring the guiding elements to a selected tooth or teeth in the maxillary and mandibular jaws on one side of the dental arch, at least one of the guiding elements being continuously adjustable in a direction substantially along the anterior-posterior axis of the dental arch and lockable in any desired position, wherein the guiding elements are configured so that the cooperating contact therebetween exerts automatically a pushing force in a direction of relative displacement between the maxillary and mandibular jaws for assuming the correct relative position between the jaws.

2. The apparatus of claim 1, wherein both of the guiding elements are continuously adjustable in the direction substantially along the antero-posterior axis of the dental arch and lockable in any desired position.

3. The apparatus of claim 1, further including a second pair of guiding elements anchorable to selected teeth in the maxillary and mandibular jaws on the other side of the dental arch from the first pair of guiding elements.

4. The apparatus of claim 1, further including means for resisting the closing movement of the jaws.

5. The apparatus of claim 4, wherein the resisting means includes a leaf spring extending from one of the guiding elements and an abutment element on the other of the guiding elements, the leaf spring being configured to engage the abutment element between a second pre-set intermediate closure position of the jaws and the complete closure position.

6. The apparatus of claim 1, further including means for releasing stress in the dental arch generated by the pushing force to the palate of the patient.

7. The apparatus of claim 6, wherein the means for releasing the stress includes a palatal button affixed to the dental arch by separate anchorings attachable to teeth in the maxillary or mandibular jaws that are independent of the selected tooth or teeth to which the anchoring means are attached.

8. The apparatus of claim 1, wherein the first pair of guiding elements is anchorable to the teeth of the maxillary and mandibular jaws in a first orientation to correct a Class II malocclusion and in a second orientation to correct a Class III malocclusion.

9. An apparatus for correcting the relative position between the maxillary and the mandibular jaws in a patient, comprising:

a first pair of guiding elements, the guiding elements being disconnected from each other when the jaws are in an open position and being in cooperating contact between a first pre-set intermediate closure position of the jaws and a complete closure position of the jaws; and means for anchoring the guiding elements to a selected tooth or teeth in the maxillary and mandibular jaws on one side of the dental arch, at least one of the guiding elements being continuously adjustable in a direction substantially along the anterior-posterior axis of the dental arch and lockable in any desired position, wherein one of the guiding elements includes a cam member and the other of the guiding elements includes a transversely extending stop member, the cam member sweeping gradually from a fixed end portion extending substantially perpendicular to the occlusion plane in a direction of closure of the jaws to a free end portion extending substantially parallel to the occlusion plane, the cam member including an extrados surface configured for cooperative sliding engagement with the transversely extending stop member to exert automatically a pushing force for assuming the correct relative position between the jaws.

10. The apparatus of claim 9, wherein the transverse stop member includes a median groove configured for receiving and guiding the extrados surface of the cam member.

11. The apparatus of claim 9, wherein at least one of the cam member and the stop member is slidably mounted on an elongated arm that extends from the anchoring means in the direction substantially along the antero-posterior axis of the dental arch.

12. The apparatus of claim 11, wherein the guiding element that includes the cam member is anchorable to a molar, and wherein the elongated arm extends anteriorly from the molar a sufficient distance to allow the extrados surface of the cam member mounted on the arm to cooperatively engage the transverse stop member at a location anteriorly of the molar.

13. The apparatus of claim 12, wherein the molar is a first molar of the maxillary or mandibular jaw, and the cam member cooperatively engages the transverse stop member at a position proximate the bicuspids.

14. The apparatus of claim 11, wherein the cam member is elastically mounted on the arm so that it yields in an opposite direction to the pushing force for assuming the correct relative position between the jaws.

15. The apparatus of claim 11, wherein the arm comprises a pair of closely spaced parallel guide shafts.

16. An apparatus for correcting the relative position between the maxillary and the mandibular jaws in a patient, comprising:

a first pair of guiding elements, the guiding elements being disconnected from each other when the jaws are in an open position and being in cooperating contact between a first pre-set intermediate closure position of the jaws and a complete closure position of the jaws; and means for anchoring the guiding elements to a selected tooth or teeth in the maxillary and mandibular jaws on one side of the dental arch, at least one of the guiding elements being continuously adjustable in a direction substantially along the anterior-posterior axis of the dental arch, wherein one of the guiding elements includes a cam member and the other of the guiding elements includes a transversely extending stop member, the cam member sweeping gradually from a fixed end portion extending substantially perpendicular to the occlusion plane in a direction of closure of the jaws to a free end portion extending substantially parallel to the occlusion plane, the cam member including an extrados surface configured for cooperative sliding engagement with the transversely extending stop member to exert automatically a pushing force for assuming the correct relative position between the jaws, and wherein the transverse stop member includes a small roller configured for receiving and guiding the extrados surface of the cam member.

17. The apparatus of claim 16, wherein the small roller is made of resilient material.

18. An apparatus for correcting the relative position between the maxillary and the mandibular jaws in a patient, comprising:

a first guiding element including a first anchoring element and a cam element, the first anchoring element capable of mounting the first guiding element to a first tooth in one of the maxillary and mandibular jaws; and a second guiding element including a second anchoring element and a transverse stop member, the second anchoring element capable of mounting the second guiding element to a second tooth in the other of the maxillary and the mandibular jaws, wherein the first and second guiding elements are mountable in coinciding positions of the dental arch such that the cam element and transverse stop member are disconnected from each other when the jaws are in an open position and come into cooperating contact only starting from a pre-set intermediate closure position of the jaws, the cooperating contact occurring at a location substantially anteriorly of the first tooth, wherein the first guiding element includes an elongated guide that extends from the first anchoring element anteriorly in a direction substantially along the anterior-posterior axis of the dental arch, the cam member being slidably mounted on the guide.

19. The apparatus of claim 18, wherein the first tooth is a molar of the dental arch and the cooperating contact between the cam element and the transverse stop member occurs at a location anteriorly of the molar.

20. The apparatus of claim 19, wherein the molar is a first molar of the dental arch and the cooperative contact between the cam element and the transverse stop member occurs proximate the bicuspids.

21. The apparatus of claim 18, wherein the cam member is continuously adjustable along the guide.

22. The apparatus of claim 21, wherein the cam member is lockable in any desired position along the elongated guide.

23. The apparatus of claim 18, wherein the elongated guide comprises a pair of closely spaced parallel rails.

24. The apparatus of claim 18, wherein the second guiding element includes an elongated arm that extends from the second anchoring element anteriorly in a direction substantially along the anterior-posterior axis of the dental arch, the stop member being mounted on the guide.

25. The apparatus of claim 24, wherein the elongated arm is adjustably mounted to the second anchoring means so that the transverse stop member can be adjusted to any desired position along the anterior-posterior axis of the dental arch.

26. The apparatus of claim 25, wherein the transverse stop member is lockable in any desired position along the anterior-posterior axis of the dental arch.

27. An apparatus for correcting the relative position between the maxillary and the mandibular jaws in a patient, comprising:

a first guiding element including a first anchoring element, a guide rail and a cam element, the first anchoring element capable of mounting the first guiding element to a first tooth in one of the maxillary and mandibular jaws, the cam element being mounted on the guide rail; and a second guiding element including a second anchoring element, an elongated arm and a transverse stop member, the second anchoring element capable of mounting the second guiding element to a second tooth in the other of the maxillary and the mandibular jaws, the transverse stop member being mounted on the elongated arm, wherein the first and second guiding elements are mountable in coinciding positions of the dental arch such that the cam element and transverse stop member are disconnected from each other when the jaws are in an open position and come into cooperating contact only starting from a pre-set intermediate closure position of the jaws, and wherein the cam element and transverse stop member are both continuously adjustable in position along the anterior-posterior axis of the dental arch and lockable in any desired position.

28. An apparatus for correcting the relative position between the maxillary and the mandibular jaws in a patient, comprising:

a first and a second pair of guiding elements, the guiding elements of the first and second pairs being disconnected from each other when the jaws are in an open position and coming into cooperating contact only starting from a pre-set intermediate closure position of the jaws, the guiding elements of the first and second pairs configured to cooperate starting from the intermediate closure position to exert a pushing force in a direction substantially along the anterior-posterior axis of the dental arch to correct an overbite or underbite condition;

means for anchoring the first and second pairs of guiding elements to a selected teeth in the maxillary and mandibular jaws on opposite sides of the dental arch wherein at least one of the guiding elements is continuously adjustable in the direction substantially along the anterior-posterior axis of the dental arch and lockable in any desired position; and a spreading element mounted in the median zone of the palate and capable of exerting a pushing force in a direction transverse to the anterior-posterior axis to spread the opposite sides of the dental arch.

29. The apparatus of claim 28, wherein the force applied by the spreading element is adjustable.

* * * * *